United States Patent [19]

Makovec et al.

[11] 4,272,538
[45] Jun. 9, 1981

[54] 5-NITRO-IMIDAZOLE WITH ANTIPROTOZOIC ACTIVITY

[75] Inventors: Francesco Makovec; Paolo Senin, both of Monza; Luigi Rovati, S. Fruttuoso di Monza, all of Italy

[73] Assignee: Rotta Research Laboratorium S.p.A., San Fruttuoso de Monza, Italy

[21] Appl. No.: 40,369

[22] Filed: May 18, 1979

[30] Foreign Application Priority Data

May 29, 1978 [IT] Italy ............................... 68223 A/78

[51] Int. Cl.³ .................. A61K 31/495; C07D 403/06
[52] U.S. Cl. ..................................... 424/250; 544/370
[58] Field of Search ......................... 544/370; 424/250

[56] References Cited

U.S. PATENT DOCUMENTS 3,794,651  2/1974  Helsley et al. ...................... 544/370

Primary Examiner—Anton H. Sutto
Assistant Examiner—James H. Turnipseed
Attorney, Agent, or Firm—Sughrue, Rothwell, Mion, Zinn and Macpeak

[57] ABSTRACT 5-nitro-imidazole derivatives of the formula

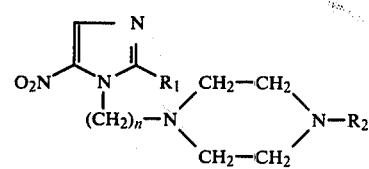

in which $R_1$ is hydrogen, methyl, ethyl or phenyl, n is 2 or 3, and $R_2$ is methyl, ethyl, carboxymethyl or carboxyethyl, and the pharamceutically acceptable acid addition salts thereof, useful as antiprotozoics.

10 Claims, No Drawings

5-NITRO-IMIDAZOLE WITH ANTIPROTOZOIC ACTIVITY

DESCRIPTION

The present invention relates to new 5-nitro-imidazole derivatives with anti-protozoic activity.

It is known to use nitro-imidazole derivatives in the treatment of humans against infections induced by protozoa, such as amoebae and trichomonas, and particularly Entamobea Histolytica, the pathogenic agent responsible for infections such as intestinal amoebiasis and hepatic abscess, and Trichomonas Vaginalis which is responsible for vulvovaginitis, urethritis, etc.

The chemio-therapeutic activity of these known nitro-imidazole derivatives, which has led to their choice, to date, for treatment of the above infections in humans, has been correlated with the potential of the nitro group present in their molecular structure for reduction; this group may, however, also be responsible for one of their particularly disadvantageous characteristics, that is, their mutagenic activity.

These disadvantages are avoided with the compounds of the present invention which have been shown to have extremely favourable pharmacological characteristics since, as well as having a strong anti-protozoic activity in experiments carried out both "in vivo" and "in vitro", they also show an extremely low level of mutagenic activity compared with the drugs most widely used, in practice, in human therapy for protozoic infections, all of which drugs belong to the family of the nitro-imidazole derivatives.

Thus, the invention provides new 5-nitro-imidazole derivatives having the general formula:

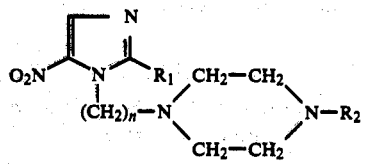

in which:
$R_1$ is hydrogen, methyl, ethyl or phenyl,
$R_2$ is methyl, ethyl, carboxymethyl or carboxyethyl, and n is 2 or 3, in the free form or in the form of a salt with a pharmaceutically acceptable acid, such as oxalic, maleic or hydrochloric acid.

The 5-nitro-imidazole derivatives of the invention may be prepared by reacting a metal salt of a 4(5)-nitro-imidazole of the formula:

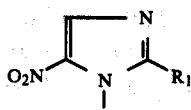

with a chloride of the formula:

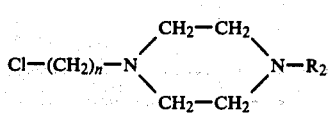

in which $R_1$, n and $R_2$ have the same meaning as above, in the presence of an anhydrous non-hydroxylic organic solvent for said derivative and at a temperature not exceeding 150° C., and recovering the derivative thus obtained from the reaction mixture, said derivative being then optionally salified by reaction with a pharmaceutically acceptable acid.

Examples of suitable organic solvents are chloroform, benzene, toluene, xylene and dimethyl sulfoxide, toluene being generally preferred.

The metal salt is conveniently an alkali metal salt, and preferably a sodium salt.

The reaction is conveniently carried out at elevated temperature and preferably at the reflux temperature, but, however, at a temperature not exceeding 150° C. The reaction time is preferably from 12 to 72 hours and typically about 48 hours.

The derivative may be recovered from the reaction mixture by filtering the latter, possibly upon cooling, distilling off the solvent at subatmospheric pressure from the filtrate thus obtained, and isolating said derivative from the distillation residue by cooling and, if necessary, by addition of a precipitating agent, and filtration. If necessary the derivative may be further purified by distillation under vacuum. Examples of suitable precipitating agents are ethers, such as ethyl and isopropyl ethers, and mixtures of ethyl acetate and ligroin.

The derivative may be salified by reaction with a pharmaceutically acceptable acid, such as oxalic, maleic or hydrochloric acid.

The general method of preparation described above will be illustrated in greater detail by the following preparation examples.

EXAMPLE 1

1-methyl-4-[3-(5-nitro-1-H-imidazol-1-yl)-propyl]-piperazine 13.5 g (0.1 moles) of the sodium salt of 4(5)-nitro-imidazole and 17.6 g (0.1 moles) of 1-methyl-4(3-chloropropyl)-piperazine are admixed with 250 cc of anhydrous toluene and the mixture is brought to reflux temperature under agitation for 48 hours. After cooling, the reaction mixture is filtered and the toluene is evaporated under vacuum from the filtrate. An oily residue is obtained from which the desired reaction product is precipitated by the addition of a small quantity of isopropyl ether.

The product may be further purified by distillation: b.p.: 125°–128° C. (0.01 mmHg); m.p.: 53°–55° C. Yield: 63%.

| Microanalysis ($C_{11}H_{19}N_5O_2$): | C% | H% | N% |
|---|---|---|---|
| calculated: | 52.15 | 7.56 | 27.64 |
| found: | 51.85 | 7.34 | 27.62 |

The free base may be salified; for this purpose it may be dissolved in acetone and precipitated in salified form by adding a solution of hydrochloric acid in acetone. The product is recrystallised from ethanol. m.p. of the hydrochloride: 261°–264° C.

EXAMPLE 2

1-ethyl-4-[3-(5-nitro-1-H-imidazol-1-yl)-propyl]-piperazine

This is carried out as in Example 1, 1-ethyl-4-(3-chloropropyl)-piperazine being used in place of 1-methyl-4(3-chloropropyl)-piperazine.

m.p.: 41°–46° C.
Yield: 60%.

| Microanalysis ($C_{12}H_{21}N_5O_2$) | C% | H% | N% |
|---|---|---|---|
| calculated: | 53.91 | 7.91 | 26.19 |
| found: | 53.60 | 7.54 | 26.30 |

EXAMPLE 3

1-carboxyethyl-4-[3-(5-nitro-1-H-imidazol-1-yl)-propyl]-piperazine

This is carried out as in Example 1 using 1-carboxyethyl-4-(3-chloropropyl)-piperazine in place of 1-methyl-4(3-chloropropyl)-piperazine.
m.p.: oil, m.p. of the hydrochloride 231°–233° C.
Yield 74%.

| Microanalysis (dihydrochloride) | C% | H% | N% |
|---|---|---|---|
| $C_{13}H_{23}Cl_2N_5O_4$ |  |  |  |
| calculated | 40.63 | 6.03 | 18.23 |
| found | 40.81 | 5.75 | 18.00 |

EXAMPLE 4

1-methyl-4-[2-(5-nitro-1-H-imidazol-1-yl)-ethyl]-piperazine

This is carried as in Example 1, using 1-methyl-4-(2-chloroethyl)-piperazine in place of the 1-methyl-4-(3-chloropropyl)-piperazine.
m.p.: 56°–61° C., b.p.=134°–138° C. (0.01 mmHg).
Yield 58%.

| Microanalysis ($C_{10}H_{17}N_5O_2$) | C% | H% | N% |
|---|---|---|---|
| calculated: | 50.19 | 7.16 | 29.27 |
| found: | 50.04 | 6.93 | 29.51 |

EXAMPLE 5

1-carboxyethyl-4-[2-(5-nitro-1-H-imidazol-1-yl)-ethyl]-piperazine

This is carried as in Example 1 using 1-carboxyethyl-4-(2-chloroethyl)-piperazine in place of 1-methyl-4(3-chloropropyl)-piperazine.
m.p.: oil; m.p. of the hydrochloride: 236°–239° C.
Yield 66%.

| Microanalysis (dihydrochloride): | C% | H% | N% |
|---|---|---|---|
| $C_{12}H_{21}Cl_2N_5O_4$ |  |  |  |
| calculated: | 38.93 | 5.72 | 18.92 |
| found | 39.40 | 5.80 | 19.07 |

EXAMPLE 6

1-methyl-4-[3-(2-methyl-5-nitro-1-H-imidazol-1-yl)-propyl]-piperazine

This is carried out as in Example 1 using the sodium salt of 2-methyl-4-(5)-nitro-imidazole in place of the sodium salt of 4(5)-nitro-imidazole.
m.p.: 74°–76° C.; b.p.=171°–174° C. (0.05 mmHg).
m.p. of the hydrochloride: 226°–228° C.
Yield: 61%.

| Microanalysis ($C_{12}H_{21}N_5O_2$): | C% | H% | N% |
|---|---|---|---|
| calculated: | 53.91 | 7.91 | 26.19 |
| found: | 53.70 | 7.77 | 26.11 |

EXAMPLE 7

1-carboxymethyl-4-[3-(2-methyl-5-nitro-1-H-imidazol-1-yl)-propyl]-piperazine

This is carried out as in Example 1 using, in this case, the sodium salt of 2-methyl-4(5)-nitro-imidazole and 1-carboxymethyl-4-(3-chloropropyl)-piperazine.
m.p.: oil; m.p. of the hydrochloride: 244°–248° C.
Yield: 66%.

| Microanalysis ($C_{13}H_{21}N_5O_4$): | C% | H% | N% |
|---|---|---|---|
| calculated: | 50.15 | 6.79 | 22.49 |
| found: | 49.70 | 6.43 | 22.01 |

EXAMPLE 8

1-carboxyethyl-4-[3-(2-methyl-5-nitro-1-H-imidazol-1-yl)-propyl]-piperazine

This is carried out as in Example 1 using, in this case, the sodium salt of 2-methyl-4(5)-nitro-imidazole and 1-carboxyethyl-4-(3-chloropropyl)-piperazine.
m.p.: oil; m.p. of the hydrochloride: 237°–240° C.
Yield: 70%.

| Microanalysis ($C_{14}H_{23}N_5O_5$): | C% | H% | N% |
|---|---|---|---|
| calculated: | 51.67 | 7.12 | 21.52 |
| found: | 50.33 | 6.75 | 21.20 |

EXAMPLE 9

1-methyl-4-[2-(2-methyl-5-nitro-1-H-imidazol-1-yl)-ethyl]-piperazine

This is carried out as Example 1, using, in this case, the sodium salt of 2-methyl-4(5)-nitro-imidazole and 1-methyl-4-(2-chloroethyl)-piperazine.
m.p.: 61°–64° C.; b.p.=170°–173° C. (0.1 mmHg).
Yield: 57%.

| Microanalysis($C_{11}H_{19}N_5O_2$): | C% | H% | N% |
|---|---|---|---|
| calculated: | 52.15 | 7.56 | 27.64 |
| found: | 52.32 | 7.40 | 27.13 |

EXAMPLE 10

1-methyl-4-[3-(2-ethyl-5-nitro-1-H-imidazol-1-yl)-propyl]-piperazine

This is carried out as in Example 1 using sodium salt of 2-ethyl-4(5)-nitro-imidazole in place of the sodium salt of 4(5)-nitro-imidazole.
m.p.: 36°–42° C.
Yield: 50%.

| Microanalysis ($C_{13}H_{23}N_5O_2$): | C% | H% | N% |
|---|---|---|---|
| calculated: | 55.49 | 8.23 | 24.89 |
| found: | 55.60 | 8.01 | 24.20 |

EXAMPLE 11

1-methyl-4-[3-(2-phenyl-5-nitro-1-H-imidazol-1-yl)-propyl]-piperazine

This is carried out as in Example 1 using the sodium salt of 2-phenyl-4(5)-nitro-imidazole in place of the sodium salt of 4(5)-nitro-imidazole.
m.p.: oil; b.p.=196°-200° C. (0.04 mmHg).
m.p. of the hydrochloride: 226°-229° C.
Yield: 44%.

| Microanalysis ($C_{17}H_{23}N_5O_2$): | C% | H% | N% |
|---|---|---|---|
| calculated: | 61.98 | 7.03 | 21.26 |
| found: | 61.74 | 6.85 | 20.90 |

EXAMPLE 12

1-methyl-4-[2-(2-phenyl-5-nitro-1-H-imidazol-1-yl)-ethyl]-piperazine

This is carried as in Example 1 using in this case the sodium salt of 2-phenyl-4(5)-nitro-imidazole and 1-methyl-(2-chloroethyl)-piperazine.
m.p.: oil; b.p.=203°-208° C. (0.04 mmHg).
m.p. hydrochloride: 236°-240° C.
Yield: 40%.

| Microanalysis ($C_{16}H_{21}N_5O_2$): | C% | H% | N% |
|---|---|---|---|
| calculated: | 60.93 | 6.71 | 22.20 |
| found: | 59.83 | 6.40 | 22.22 |

(A) Activity "in vitro"

The method of evaluation of the activity of the compounds of the invention "in vitro" consists of introducing various quantities of the substance to be tested, into a culture medium previously inoculated with a predetermined number of test germs.

After 48 hours of incubation at 37° C. it is possible to evaluate the growth of the micro-organism in the culture broth; thus the minimum concentration (M.I.C.) which inhibits the growth of the microorganisms "in vitro" is determined.

($A_1$) Trichomonas Vaginalis

The Trichomonas Vaginalis stocks are kept vital by transfer every 48 hours into Trichosel BBL substrate containing 15% in weight/volume of deactivated horse serum. The composition of the Trichosel BBL substrate is disclosed for example in Exp. Biol. and Med., Vol. 67, p. 304 (1948).

The inoculation was carried out in the proportion of 5% of the volume of the above substrate, to which has been added 5% in weight/volume of horse serum. The evaluation is macroscopic, the presence or lack of live cells in the culture medium being observed.

pH of the inoculated culture medium: 6.0.

($A_2$) Entamoeba Histolytica

The stock is kept vital by transfer every 48 hours at 37° C. into slants containing a bi-phase medium composed of 5 ml of coagulated horse serum and 50 ml of Pavlova substrate containing 15% in weight/volume of deactivated horse serum. The Pavlova substrate is described for example in Ann. Trop. Med. Parasitology, Vol. 40, p. 130 (1946).

The measurement of the M.I.C. is carried out in test tubes containing 0.5 ml of coagulated horse serum and the liquid phase of the Pavlova substrate containing 5% in weight/volume of horse serum, previously inoculated in the proportion of about 10,000 cells per ml of substrate.

The evaluation is microscopic, the presence or lack of live cells in the culture medium being observed.

The results obtained are recorded in Table 1 which shows the activity in vitro (M.I.C.) of the compounds of the invention against Trichomonas Vaginalis and Entamoeba Histolytica. The values given are average values (A), the respective standard errors (S.E.) being calculated from series of 5 tests for each product; values of Student's "t" which relates to the comparison of the averages obtained for the individual compounds and for metronidazole are also given.

TABLE 1

Antitriohomonas and Anti-amoebic activity in vitro, expressed as minimum inhibiting concentration (M.I.C.) in γ/ml of culture broth.

| COMPOUND | SUBSTITUTUENTS | | | TRICHOMONAS VAGINALIS ISM 66/22 | | E. HISTOLYTICA | |
|---|---|---|---|---|---|---|---|
| | $R_1$ | n | $R_2$ | M.I.C. γ/ml A ± S.E. | t | M.I.C. γ/ml A ± S.E. | t |
| Example 1 | H | 3 | $CH_3$ | 6.30 ± 1.37 | 3.54 <0.01 | 51.2 ± 43.1 | N.S. |
| Example 2 | H | 3 | $-C_2H_5$ | 5.80 ± 1.12 | 3.81 <0.01 | 60.1 ± 14.2 | N.S. |
| Example 3 | H | 3 | $-COOC_2H_5$ | 0.56 ± 0.10 | 1.99 N.S. | 53.1 ± 11.5 | N.S. |
| Example 4 | H | 2 | $-CH_3$ | 7.90 ± 1.37 | 4.65 <0.01 | 63.1 ± 14.2 | N.S. |
| Example 5 | H | 2 | $-COOC_2H_5$ | 2.40 ± 0.70 | 1.41 N.S. | 66.1 ± 16.0 | N.S. |
| Example 6 | $-CH_3$ | 3 | $-CH_3$ | 3.2 ± 0.82 | 2.13 N.S. | 22.0 ± 8.5 | N.S. |
| Example 7 | $-CH_3$ | 3 | $-COOCH_3$ | 2.20 ± 0.85 | 0.98 N.S. | 45.0 ± 11.5 | N.S. |
| Example 8 | $-CH_3$ | 3 | $-COOC_2H_5$ | 0.70 ± 0.13 | 1.59 N.S. | 40.1 ± 10.8 | N.S. |
| Example 9 | $-CH_3$ | 2 | $-CH_3$ | 3.40 ± 1.00 | 1.97 N.S. | 26.0 ± 8.0 | N.S. |
| Example 10 | $-C_2H_5$ | 3 | $-CH_3$ | 2.70 ± 0.85 | 1.52 N.S. | 26.0 ± 10.4 | N.S. |

TABLE 1-continued

Antitriohomonas and Anti-amoebic activity in vitro, expressed as minimum inhibiting concentration (M.I.C.) in γ/ml of culture broth.

| COMPOUND | SUBSTITUTUENTS $R_1$ | n | $R_2$ | TRICHOMONAS VAGINALIS ISM 66/22 M.I.C. γ/ml A ± S.E. | t | E. HISTOLYTICA M.I.C. γ/ml A ± S.E. | t |
|---|---|---|---|---|---|---|---|
| Example 11 | ⟨phenyl⟩ | 3 | —CH$_3$ | 5.60 ± 1.28 | 3.24 <0.02 | 39.0 ± 12.6 | N.S. |
| Example 12 | ⟨phenyl⟩ | 2 | —CH$_3$ | 8.1 ± 2.10 | 3.18 <0.02 | 43.0 ± 9.8 | N.S. |
| METRONIDAZOLE | — | — | — | 1.30 ± 0.356 | — | 25.0 ± 10.12 | — |
| NIRIDAZOLE | — | — | — | 1.22 ± 0.411 | 0.15 N.S. | 28.0 ± 9.6 | N.S. |
| TINIDAZOLE | — | — | — | 0.66 ± 0.11 | 1.71 N.S. | 32.0 ± 11.5 | N.S. |

Note:
N.S.: Not significant

By examining the results of Table 1, it may be noted that the compounds under examination exert their antiprotozoic activity at very low concentrations, similar to those of the better known drugs actually used in human therapy. In fact, in most cases there are no statistically significant differences between the antiprotozoic activity in vitro of the compounds of the invention and that of the control drugs.

Generally the best results are obtained with $R_1$=H, CH$_3$, n=3 and $R_2$=CH$_3$ or COOC$_2$H$_5$ where $R_1$, n and $R_2$ have the same meaning as described hereinbefore.

(B) Activity in vivo

The activity of the compounds described in the Examples against Trichomonas Vaginalis and Entamoeba Histolytica was tested in vivo in order to ascertain whether the activity shown by these compounds against protozoic cultures in vitro would also be manifested against experimental infections in vivo in conditions approaching (especially for experimental hepatic abscess) the pathological conditions which require the use of a drug with anti-protozoic activity in human therapy.

(B$_1$) Systematic activity in mice infected subcutaneously with Trichomonas Vaginalis Female Charles River mice of about 20 grams weight are used and injected subcutaneously with 1 ml of a physiological solution containing 10$^6$ cells of Trichomonas Vaginalis (evaluated by means of counting in a Burker chamber), resulting from a 24 hour culture in Trichosel BBL substrate containing 15% in weight/volume of deactivated horse serum.

Abscesses are thus developed in the place of infection which may burst open externally, piercing the skin.

To establish the activity of a product, groups of 10 animals per tested dose are used, and on the 7th day the presence or absence of abscesses are determined (evaluated in terms of all or nothing). The compounds are administered orally, dissolved or in suspension in water, over 5 days, twice a day, the treatment being started 30 minutes after infection.

The results obtained are recorded in Table 2 which gives the ED$_{84}$ in mg/kg for oral administration, that is the dose of the drug capable of preventing the formation of the infection in 84% of the infected animals. The values of the ED$_{84}$ given were calculated from the regression line obtained from the results of a series of experiments, each compound being administered to at least 5 groups of 10 animals at generally different doses. An index of the relative activity, that is, the activity of the compounds of the invention compared with the activity of metronidazole is also given.

TABLE 2

Anti-trichomonas activity in mice (Oral administration - experimental subcutaneous infection)

| Compound | No. of animals used | ED$_{84}$ | Index of relative activity $\left(\dfrac{\text{Metronidazole}}{\text{compounds}}\right)$ Calc. on ED$_{84}$ |
|---|---|---|---|
| Example 1 | 90 | 69.4 (S) | 0.41 |
| Example 2 | 50 | 66.0 (NS) | 0.43 |
| Example 3 | 100 | 170.5 (S) | 0.16 |
| Example 4 | 50 | 77.5 (NS) | 0.37 |
| Example 6 | 80 | 41.2 (S) | 0.69 |
| Example 8 | 50 | 150.2 (NS) | 0.19 |
| Example 9 | 50 | 60.5 (S) | 0.47 |
| Example 10 | 50 | 30.7 (NS) | 0.93 |
| Example 11 | 50 | 48.0 (NS) | 0.59 |
| Metronidazole | 120 | 28.7 (S) | 1 |
| Nimorazole | 50 | 62.6 (NS) | 0.45 |

Note:
S (significant) when the coefficient of correlation (p) relative to the calculated regression line is less than 0.05.
N.S. (not significant) when said coefficient of correlation is higher than 0.05.

From examination of Table 2, it is noted that the new compounds under consideration have more or less the same degree of activity as the known compounds chosen for reference; for several, however, such as, for example, the compounds of Examples 3 and 8, which are very active in vitro, the activity is reduced, which may be interpreted as being due to poor peripheral absorption which would prejudice their use in this type of experiment.

(B$_2$) Systemic activity on hepatic abscess from Entamoeba Histolytica in the hamster Golden hamsters of the strain RRL-805 of about 50 grams weight are used; after laparatomy, 0.05 ml of a suspension of amoebae (cellular density of about 10$^6$ amoebae/ml) is injected into the right hepatic lobe. Abscesses develop on the liver, the average weight of which is determined after killing of the animals 72 hours after the injection.

The drugs under examination are administered orally twice a day for four days, the treatment being started the day before the infection.

The evaluation is carried out by comparing the average weight of the hepatic abscesses developed in the group of animals treated with a drug with that of a control group.

The results obtained are recorded in Table 3 which gives the $ED_{84}$ in mg/kg administered orally, that is the dose of the drug capable of reducing the weight of the abscesses by 84% with respect to the controls.

The values given were calculated from the regression line obtained from the results of a series of experiments, each compound being administered to at least 5 groups of six animals at generally different doses. An index of the relative activity of the compounds as compared to that of metronidazole is also given.

TABLE 3

Anti-amoebic activity in the hamster
(Oral administration - experimental infection in the liver)

| Compound | No. animals used | $ED_{84}$ | Index of relative activity $\left(\dfrac{\text{metronidazole}}{\text{compounds}}\right)$ Calc. on the $ED_{84}$ |
|---|---|---|---|
| Example 1 | 36 | 86.3 (S) | 1.2 |
| Example 3 | 30 | 84.7 (NS) | 1.2 |
| Example 4 | 30 | 107.7 (NS) | 1 |
| Example 6 | 42 | 54.2 (S) | 2 |
| Example 8 | 36 | 75.5 (S) | 1.4 |
| Example 9 | 30 | 77.1 (NS) | 1.4 |
| Example 11 | 30 | 130.3 (S) | 0.8 |
| Metronidazole | 48 | 108.0 (S) | 1 |
| Nimorazole | 30 | 132.9 (NS) | 0.8 |
| Tinidazole | 30 | 98.0 (NS) | 1.1 |

S = significant
NS = non significant
(See note given under Table 2).

As may be seen from examination of Table 3, the compound of Example 6 shows the greatest activity in this test which is not easy to carry out or to reproduce (the coefficients of correlation obtained are not always reliable) and it has about twice the activity of metronidazole; other compounds of the invention are also more active than the control compounds.

Toxicity

The acute oral toxicity of the compounds according to the invention was also determined in mice and compared with that of other nitro-imidazole compounds used previously as control standards.

For every dose tested, the substance was administered orally to groups of 10 female $CF_1$ mice, having an average weight of about 20 grams, in an aqueous suspension containing 10% of gum arabic, the volume administered being 1 ml/100 grams of body weight. The $LD_{50}$ was determined, that is, the dose expressed in mg/kg of body weight which induces the death of 50% of the animals treated within 14 days from administration.

TABLE 4

| Acute oral toxicity in mice expressed as $LD_{50}$ in mg/kg | |
|---|---|
| COMPOUND | $LD_{50}$ mg/kg |
| Example 1 | 810 |
| Example 2 | 900 |
| Example 3 | 2430 |
| Example 4 | 880 |
| Example 5 | 2310 |
| Example 6 | 1630 |
| Example 7 | 2420 |
| Example 8 | 2630 |

TABLE 4-continued

| Acute oral toxicity in mice expressed as $LD_{50}$ in mg/kg | |
|---|---|
| COMPOUND | $LD_{50}$ mg/kg |
| Example 9 | 1700 |
| Example 10 | 1960 |
| Example 11 | 1680 |
| Example 12 | 3320 |
| Metronidazole | 4300* |
| Nimorazole | 3180* (rat) |
| Tinidazole | 3600* |

*data from literature

As is seen from examination of Table 4, the substances under examination generally have an acute oral toxicity which is greater than that of the chosen reference compounds; however, this toxicity is relatively low and of no practical importance considering the doses envisaged for human use.

Mutagenic Nature

Mutagenesis test with metabolic activation on histidine (−) strains of Salmonella Typhimurium by the Ames method The capacity for reversing the histidine (−) mutation which is peculiar to the TA 100 strain was measured, this strain being recommended for chemio-therapeutic screening in that it has a resistance factor R; TA 100 is a carrier of a mutation caused by the substitution of a pair of bases. The method used is that described by Ames et al. (Mutation Res. 31, (1975), 347–364).

The results obtained are shown in Table 5 which gives the maximul value of revertants per plate obtained for the various concentrations tested (range of from 15.62 to 1000 μg/plate), value which allows good descrimination between the experimental value and the background of the control (which is about 100 revertants per plate).

TABLE 5:

| Mutagenic activity in the Ames test in vitro on *Salmonella Typhimurium* TA 100 | | |
|---|---|---|
| Compound | Revertants/plate (max value) | Index of relative mutagenic power (Compound/ Metronidazole) |
| Example 1 | 780 | 0.17 |
| Example 3 | 1400 | 0.31 |
| Example 4 | 780 | 0.17 |
| Example 6 | 510 | 0.11 |
| Example 8 | 1140 | 0.25 |
| Example 9 | 460 | 0.10 |
| Example 12 | 750 | 0.16 |
| Metronidazole | 4500 | 1 |
| Tinidazole | 4000 | 0.9 |

From examination of Table 5, it may be noted that the nitro-imidazole derivatives of the invention have a very low mutagenic activity, in several cases only slightly greater, than that of the background activity of the controls, and in any case from three to ten times lower than that of metronidazole, a drug which is an everyday choice for use in treating protozoic infections (from amoebae and trichomonas). This fact is probably of utmost importance, in view of the known correlation betweem mutagenic activity and carcinogenic activity.

The compounds of the present invention may advantageously be used in human therapy in mixture with suitable carriers or excipients which are acceptable from the pharmacological point of view.

For example, against vaginitis and urethritis due to Trichomonas Vaginalis or intestinal amoebiasis or hepatic amoebic abscess, the compounds of the invention, and preferably 1-methyl-4-[3-(2-methyl-5-nitro-1-H-imidazol-1-yl)-propyl]-piperazine (Example 6), 1-methyl-4-[3-(5-nitro-1-H-imidazol-1-yl)-propyl]-piperazine (Example 1), 1-carboxyethyl-4-[5-nitro-1-H-imidazol-1-yl)-propyl]-piperazine (Example 3), may advantageously be administered orally in tablets or capsules containing from 100 to 500 mg of compound, up to a maximum administration of 2000 mg per day and for a period of up to two weeks in the more difficult cases, whereas in the less serious cases, one or two days of therapy may be sufficient. In the more difficult cases of vaginitis and urethritis, in addition to the general treatment, a local treatment may also be carried out by means of the administration of vaginal suppositories while adhering to the dosage indicated above.

We claim:

1. A compound selected from the group consisting of compounds having the formula:

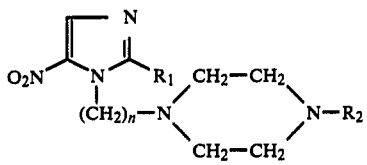

in which $R_1$ is hydrogen, methyl, ethyl or phenyl, n is 2 or 3, and $R_2$ is methyl, ethyl, carboxymethyl or carboxyethyl, and the pharmaceutically acceptable acid addition salts thereof.

2. The compound of claim 1, wherein said pharmaceutically acceptable acid addition salts are selected from the group consisting of the acid salts of oxalic, maleic and hydrochloric acids.

3. The compound of claim 1, consisting of 1-methyl-4-[3-(5-nitro-1-H-imidazol-1-yl)-propyl]-piperazine.

4. The compound of claim 1, consisting of 1-carboxyethyl-4-[3-(5-nitro-1-H-imidazol-1-yl)-propyl]-piperazine.

5. The compound of claim 1, consisting of 1-methyl-4-[3-(2-methyl-5-nitro-1-H-imidazol-1-yl)-propyl]-piperazine.

6. The compound of claim 1, consisting of 1-methyl-4-[3-(2-phenyl-5-nitro-1-H-imidazol-1-yl)-propyl]-piperazine.

7. An anti-protozoic pharmaceutical preparation comprising a compound according to claim 1, as the active ingredient, and a pharmaceutically acceptable carrier or diluent.

8. The preparation of claim 7, wherein said compound is 1-methyl-4-[3(2-methyl-5-nitro-1-H-imidazol-1-yl)-propyl]-piperazine.

9. The preparation of claim 7, wherein said compound is 1-methyl-4-[3-(5-nitro-1-H-imidazol-1-yl)-propyl]-piperazine.

10. The preparation of claim 7, wherein said compound is 1-carboxyethyl-4[3-(5-nitro-1-H-imidazol-1-yl)-propyl]-piperazine.

* * * * *